United States Patent [19]
Brieden et al.

[11] Patent Number: 6,160,115
[45] Date of Patent: Dec. 12, 2000

[54] PROCESS FOR PREPARING N-[5-(DIPHENYLPHOSPHINOYLMETHYL)-4-(4-FLUOROPHENYL)-6-ISOPROPYLPYRIMIDIN-2-YL]-N-METHYLMETHANESULFONAMIDE

[75] Inventors: Walter Brieden, Brig-Glis; Ulrich Veith, Visp, both of Switzerland

[73] Assignee: Lonza AG, Basel, Switzerland

[21] Appl. No.: 09/521,842

[22] Filed: Mar. 9, 2000

Related U.S. Application Data

[60] Provisional application No. 60/147,139, Aug. 4, 1999.

[30] Foreign Application Priority Data

Mar. 10, 1999 [EP] European Pat. Off. .............. 99104786

[51] Int. Cl.[7] ....................................................... C07D 9/53
[52] U.S. Cl. ........................................... 544/243; 544/297
[58] Field of Search ...................... 544/243, 297

[56] References Cited

FOREIGN PATENT DOCUMENTS

0521471 A1  1/1993  European Pat. Off. .

OTHER PUBLICATIONS

Bioorg. Med. Chem., 1997, 5, 437.

Primary Examiner—John M. Ford
Attorney, Agent, or Firm—Fisher, Christen & Sabol

[57] ABSTRACT

N-[5-(Diphenylphosphinoylmethyl)-4-(4-fluorophenyl)-6-isopropylpyrimidin-2-yl]-N-methylmethanesulfonamide of the formula:

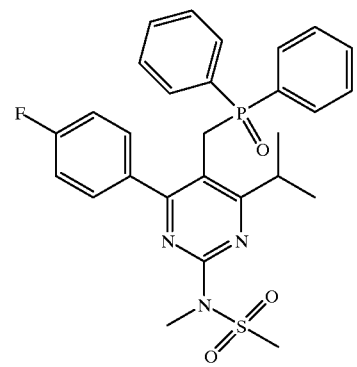

I is prepared by reaction of [4-(4-fluorophenyl)-6-isopropyl-2-(N-methyl-N-methylsulfonylamino)pyrimidin-5-yl] methanol with chlorodiphenylphosphine. Compound I is an intermediate in the synthesis of pharmaceutically active compounds, in particular HMG—Co A. reductase inhibitors.

16 Claims, No Drawings

PROCESS FOR PREPARING N-[5-(DIPHENYLPHOSPHINOYLMETHYL)-4-(4-FLUOROPHENYL)-6-ISOPROPYLPYRIMIDIN-2-YL]-N-METHYLMETHANESULFONAMIDE

This appln claims the benefit of U.S. Provisional No. 60/147,139 filed Aug. 4, 1999.

BACKGROUND OF THE INVENTION

The present invention relates to a process for preparing N-[5-(diphenylphosphinoylmethyl)-4-(4-fluorophenyl)-6-isopropylpyrimidin-2-yl]-N-methylmethanesulfonamide:

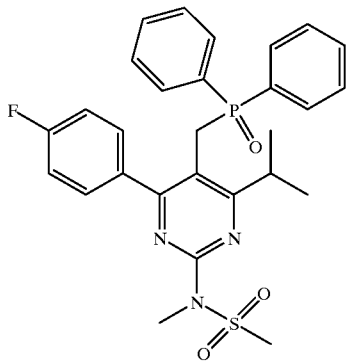

I

It is the object of the invention to provide better access to the abovementioned intermediate. The object is achieved by the novel process according to the invention.

According to the invention, N-[5-(diphenylphosphinoylmethyl)-4-(4-fluorophenyl)-6-isopropylpyrimidin-2-yl]-N-methylmethanesulfonamide of the formula (I) is prepared by reacting [4-(4-fluorophenyl)-6-isopropyl-2-(N-methyl-N-methyl-sulfonyl-amino)pyrimidin-5-yl]methanol of the formula (II):

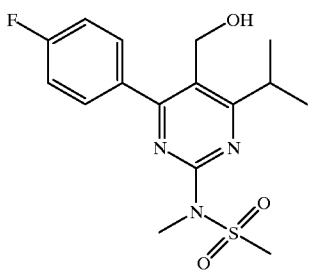

II with chlorodiphenylphosphine.

The N-[5-(diphenylphosphinoylmethyl)-4-(4-fluorophenyl)-6-isopropylpyrimidin-2-yl]-N-methylmethanesulphonamide (I) preparable according to the invention is an intermediate for the preparation of pharmaceutically active compounds, for example of HMG—Co A reductase inhibitors (Bioorg. Med. Chem. 1997, 5, 437).

An important advantage of the synthesis according to the invention is its industrial applicability.

DETAILED DESCRIPTION OF THE INVENTION

[4-(4-Fluorophenyl)-6-isopropyl-2-(N-methyl-N-methylsulfonylamino)pyrimidin-5-yl]methanol of the formula (II) can be obtained in a simple manner by reducing the corresponding ester, for example, with diisobutylaluminium hydride (EP-A 0521471).

The reaction of the [4-(4-fluorophenyl)-6-isopropyl-2-(N-methyl-N-methylsulfonylamino)pyrimidin-5-yl]methanol of the formula (II) with chlorodiphenylphosphine can be carried out either directly or via prior deprotonation. Preference is given to the direct reaction with chlorodiphenylphosphine and subsequent treatment with a base.

According to the "deprotonation" variant, the [4-(4-fluorophenyl)-6-isopropyl-2-(N-methyl-N-methylsulfonylamino)pyrimidin-5-yl]methanol of the formula (II) is advantageously treated with a deprotonating agent which is familiar to the person skilled in the art, preferably with an alkali metal hydride or an alkali metal hexaalkyldisilazane. Preference is given to using sodium hydride. The deprotonation is usually carried out at room temperature. This is followed by the reaction with chlorodiphenylphosphine. The reaction with chlorodiphenylphosphine is advantageously carried out at a temperature between 80° and 200° C.

The chlorodiphenylphosphine can act directly as solvent. However, it is possible to use additionally a very high-boiling inert solvent, such as, toluene or xylene or decalin, and the respective isomer mixtures.

The reaction can be carried out in the presence of a catalyst. Suitable catalysts are iodine, an alkali metal iodide, such as, sodium iodide or potassium iodide, an alkali metal halide, such as, methyl iodide or ethyl iodide, or a dihaloalkane, such as, dibromomethane. Preference is given to using an alkali metal iodide. The amount of catalyst is usually chosen in the range from 1 mol percent to 20 mol percent, based on the alcohol of the formula II used.

The reaction according to the direct variant is advantageously carried out at a temperature of from −20° to 130° C., preferably at from +20° to 120° C. Corresponding to the "deprotonation" variant described above, the chlorodiphenylphosphine can act in the direct variant directly as solvent. However, it is possible to use additionally a very high-boiling inert solvent, such as, toluene or xylene or decalin, and the respective isomer mixtures.

Following the reaction with chlorodiphenylphosphine, the reaction mixture is treated with a base. Suitable bases are the alkali metal hydroxides, such as, aqueous solutions of sodium hydroxide or potassium hydroxide, or alkali metal carbonates, such as, sodium carbonate or potassium carbonate. If appropriate, a customary phase-transfer catalyst, such as, a tetraalkylammonium halide, can be employed to accelerate the reaction with the base. Good results can also be obtained by using crown ethers.

After the reaction has ended, the N-[5-(diphenylphosphinoylmethyl)-4-(4-fluorophenyl)-6-isopropylpyrimidin-2-yl]-N-methylmethanesulfonamide of the formula I can be isolated from the mixture in a manner known to a person skilled in the art, for example, by extraction from the reaction mixture using a suitable solvent, and by crystallization.

EXAMPLE 1

N-[5-(Diphenylphosphinoylmethyl)-4-(4-fluorophenyl)-6-isopropylpyrimidin-2-yl]-N-methylmethanesulfonamide 1.00 g (2.83 mmol) of [4-(4-fluorophenyl)-6-isopropyl-2-(N-methyl-N-methylsulfonylamino)pyrimidin-5-yl]methanol was initially charged in 5 ml of cis/trans-decalin and admixed with 204 mg (4.68 mmol) of sodium hydride (55 percent dispersion in mineral oil). After 30 min at room temperature, 680 mg (2.93 mmol) of chlorodiphenylphosphine was added with vigorous stirring over a period of 6 min. The mixture was admixed with 52.2 mg (0.35 mmol) of sodium iodide and heated at 184° to 186° C. for 2 h, 15 min. After cooling to room temperature, 50 ml of 38 to 40 percent strength sodium bisulfite solution and 50 ml of ethyl acetate were added. The organic phase was separated off and the aqueous phase was extracted with 50 ml of ethyl acetate. The combined organic phases were dried over magnesium sulfate and concentrated under reduced pressure. This gave 1.74 g of crude product which was purified by silica gel chromatography (mobile phase: n-hexane/ethyl acetate 1:2). This gave 382.4 mg (25.1 percent) of N-[5-(diphenylphosphinoylmethyl)-4-(4-fluorophenyl)-6-isopropylpyrimidin-2-yl]-N-methylmethanesulfonamide in the form of a colorless solid. The melting point was 180° to 185° C. Other data concerning the product was:

| 1H NMR (DMSO-d6, 400 MHz): | $\delta =$ | 1.11 (d,J = 6.6 Hz, 6H); |
| --- | --- | --- |
| | | 3.28 (sept, J = 6.6 Hz, 1H); |
| | | 3.40 (s, 3H); |
| | | 3.51 (s, 3H); |
| | | 4.05 (d, J = 12.6 Hz, 2H); |
| | | 7.07 (t, J = 8.9 Hz, 2H); |
| | | 7.35 (m, 2H); |
| | | 7.42 (m, 4H); |
| | | 7.5–7.9 (m, 6H). |
| 13C NMR (DMSO-d6, 100 MHz): | $\delta =$ | 21.52 (q); |
| | | 29.12 (td); |
| | | 31.94 (d); |
| | | 33.07 (q); |
| | | 41.53 (q); |
| | | 114.50 (sd); |
| | | 115.03 (dd); |
| | | 128.54 (dd); |
| | | 130.21 (dd); |
| | | 130.84 (dd); |
| | | 131.64 (dd); |
| | | 133.41 (sd); |
| | | 134.51 (sd); |
| | | 156.54 (sd); |
| | | 162.10 (sd); |
| | | 165.86 (sd); |
| | | 176.49 (sd). |

EXAMPLE 2

N-[5-(Diphenylphosphinoylmethyl)-4-(4-fluorophenyl)-6-isopropylpyrimidin-2-yl]-N-methylmethanesulfonamide 282.8 mg (0.80 mmol) of [4-(4-fluorophenyl)-6-isopropyl-2-(N-methyl-N-methylsulphonylamino)pyrimidin-5-yl]methanol was initially charged in 4.5 ml of xylene (isomer mixture) and admixed with 55 mg (1.30 mmol) of sodium hydride (55 percent dispersion in mineral oil). After 35 min, 185 mg (0.84 mmol) of chlorodiphenylphosphine in 1.5 ml of xylene was added at room temperature with vigorous stirring over a period of 5 min, and the mixture was subsequently heated at 135° C. for 20 h. After cooling to room temperature, the mixture was admixed with 15 ml of water and extracted with 10 ml of ethyl acetate. The organic phase was separated off and the aqueous phase was extracted with 2×10 ml of ethyl acetate. The combined organic phases were subsequently dried (MgSO4) and concentrated under reduced pressure. This gave 510 mg of crude product which was purified by silica gel chromatography (mobile phase: n-hexane/ethyl acetate 1:2, then ethyl acetate), and 230 mg (53.5 percent) of N-[5-(diphenylphosphinoylmethyl)-4-(4-fluorophenyl)-6-isopropylpyrimidin-2-yl]-N-methylmethanesulphonamide was isolated in the form of a colorless solid.

EXAMPLE 3

N-[5-(Diphenylphosphinoylmethyl)-4-(4-fluorophenyl)-6-isopropylpyrimidin-2-yl]-N-methylmethanesulfonamide 512 mg (1.45 mmol) of [4-(4-fluorophenyl)-6-isopropyl-2-(N-methyl-N-methylsulfonylamino)pyrimidin-5-yl]methanol was initially charged in 8 ml of toluene and admixed with 96 mg (2.20 mmol) of sodium hydride (55 percent dispersion in mineral oil). After 1 h, 333.5 mg (1.44 mmol) of chlorodiphenylphosphine in 2.5 ml of toluene was added at room temperature with vigorous stirring over a period of 5 min. The mixture was admixed with 28.7 mg (0.19 mmol) of sodium iodide and heated at 108° C. for 22 h. After 6 h, a further 28.7 mg (0.19 mmol) of sodium iodide were added. After cooling to room temperature, the mixture was admixed with 30 ml of 38 to 40percent strength sodium bisulfite solution and extracted with 50 ml of ethyl acetate. The organic phase was separated off and the aqueous phase was extracted with 50 ml of ethyl acetate. The combined organic phases were subsequently concentrated under reduced pressure. This gave 740 mg of crude product which was purified by silica gel chromatography (mobile phase-:ethyl acetate), and 212.7 mg (27.3 percent) of N-[5-(diphenylphosphinoylmethyl)-4-(4-fluorophenyl)-6-isopropylpyrimidin-2-yl]-N-methylmethanesulfonamide was isolated in the form of a colorless solid.

EXAMPLE 4

N-[5-(Diphenylphosphinoylmethyl)-4-(4-fluorophenyl)-6-isopropylpyrimidin-2-yl]-N-methylmethanesulfonamide 502.6 mg (1.42 mmol) of [4-(4-fluorophenyl)-6-isopropyl-2-(N-methyl-N-methylsulfonylamino)pyrimidin-5-yl]methanol was initially charged in 8 ml of xylene (isomer mixture) and admixed with 96.6 mg (2.21 mmol) of sodium hydride (55 percent dispersion in mineral oil). After 1 hour, 340.8 mg (1.47 mmol) of chlorodiphenylphosphine in 2.5 ml of xylene was added at room temperature with vigorous stirring over a period of 5 min. The mixture was admixed with 34.6 mg (0.23 mmol) of sodium iodide and heated at 136° C. for 19 h. After 3 h, a further 25.1 mg of sodium iodide were added. After cooling to room temperature, the mixture was admixed with 30 ml of dilute sodium bisulfite solution and extracted with 50 ml of ethyl acetate. The organic phase was separated off and the aqueous phase was extracted with 50 ml of ethyl acetate. The combined organic phases were subsequently concentrated under reduced pressure. This gave 906 mg of crude product which was purified by silica gel chromatography (mobile phase: ethyl acetate), and 315.9 mg (41.3 percent) of N-[5-(diphenylphosphinoylmethyl)-4-(4-fluorophenyl)-6-isopropylpyrimidin-2-yl]-N-methylmethanesulfonamide was isolated in the form of a colorless solid.

EXAMPLE 5 (DIRECT REACTION)

N-[5-(Diphenylphosphinoylmethyl)-4(4-fluorophenyl)-6-isopropylpyrimidin-2-yl]-N-methylmethanesulfonamide With ice-bath cooling, 1.05 g (2.95 mmol) of [4-(4-fluorophenyl)-6-isopropyl-2-(N-methyl-N- methylsulfonylamino)pyrimidin-5-yl]methanol was initially charged in 7 g of toluene and admixed with stirring with 820 mg (3.69 mmol) of chlorodiphenylphosphine. The mixture was heated at 108° C. for 3 h. After cooling to room temperature, 553 mg (4.43 mmol) of aqueous potassium hydroxide solution (45 percent strength) and 97.5 mg (0.29 mmol) of tetrabutylammonium bromide was added, and the mixture was stirred vigorously at 60° C. for 1 h. The heat source was removed and the reaction mixture, which was still warm, was admixed with 20 ml of water. The mixture was slowly cooled to 4° C., and the precipitated solid was filtered off. The product was washed with cold water and toluene and dried under reduced pressure at 40° C. 1.04 g (64.1 percent; content: 97.6 percent) of N-[5-(diphenylphosphinoylmethyl)-4-(4-fluorophenyl)-6-isopropylpyrimidin-2-yl]-N-methylmethanesulfonamide was isolated in the form of a colorless solid.

EXAMPLE 6 (DIRECT REACTION)

N-[5-(Diphenylphosphinoylmethyl)-4-(4-fluorophenyl)-6-isopropylpyrimidin-2-yl]-N-methylmethanesulphonamide 2.03 g (5.69 mmol) of [4-(4-fluorophenyl)-6-isopropyl-2-(N-methyl-N-methylsulfonylamino)pyrimidin-5-yl] methanol was initially charged in 13 g of toluene and, with ice-bath cooling, admixed with 1.67 g (7.51 mmol) of chlorodiphenylphosphine in 2 g of toluene. The mixture was heated at 111° C. for 2.5 h. After cooling to room temperature, 1.08 g (8.66 mmol) of a 45 percent strength potassium hydroxide solution and 175 mg (0.574 mmol) of tetrabutylammonium chloride was added, and the mixture was stirred vigorously at 60° C. for 2 h. 30 ml of water was added to the warm reaction mixture. The mixture was briefly stirred at 60° C. and slowly cooled to 4° C., and the precipitated solid was filtered off. The product was washed with cold water (10 ml) and cold toluene (10 ml) and dried under reduced pressure at 40° C. 2.66 g (84.1 percent; content: 96.6 percent) of N-[5-(diphenylphosphinoylmethyl)-4-(4-fluorophenyl)-6-isopropylpyrimidin-2-yl]-N-methylmethanesulfonamide was isolated in the form of a colorless solid.

EXAMPLE 7 (DIRECT REACTION)

N-[5-(Diphenylphosphinoylmethyl)-4-(4-fluorophenyl)-6-isopropylpyrimidin-2-yl]-N-methylmethanesulfonamide 2.02 g (5.69 mmol) of [4-(4-fluorophenyl)-6-isopropyl-2-(N-methyl-N-methylsulfonylamino)pyrimidin-5-yl] methanol was initially charged in 13.1 g of toluene and, with ice-bath cooling, admixed with 1.67 g (7.51 mmol) of chlorodiphenylphosphine in 1.9 g of toluene. The mixture was heated at 109° C. for 3 h. After cooling to room temperature, 590 mg (8.94 mmol) of solid potassium hydroxide and 159 mg (0.582 mmol) of 18-crown-6 were added, and the mixture was stirred vigorously at 60° C. for 3.5 h. 30 ml of water was added to the warm reaction mixture. The mixture was briefly stirred at 60° C. and slowly cooled to 4° C., and the precipitated solid was filtered off. The product was washed with cold water (10 ml) and cold toluene (10 ml) and dried under reduced pressure at 40° C. 1.82 g (59.5 percent; content: 95.9 percent) of N-[5-(diphenylphosphinoylmethyl)-4-(4-fluorophenyl)-6-isopropylpyrimidin-2-yl]-N-methylmethanesulphonamide was isolated in the form of a colorless solid.

EXAMPLE 8 (DIRECT REACTION)

N-[5-(Diphenylphosphinoylmethyl)-4-(4-fluorophenyl)-6-isopropylpyrimidin-2-yl]-N-methylmethanesulphonamide 2.02 g (5.69 mmol) of [4-(4-fluorophenyl)-6-isopropyl-2-(N-methyl-N-methylsulfonylamino)pyrimidin-5-yl] methanol was initially charged in 13.1 g of toluene and, with ice-bath cooling, admixed with 1.71 g (7.69 mmol) of chlorodiphenylphosphine in 1.9 g of toluene. The mixture was heated at 111° C. for 2.5 h. After cooling to room temperature, 1.17 g (8.78 mmol) of 30 percent strength sodium hydroxide solution and 182 mg (0.597 mmol) of tetrabutylammonium chloride were added, and the mixture was stirred vigorously at 60° C. for 3.5 h. 30 ml of water was added to the warm reaction mixture. The mixture was briefly stirred at 60° C. and slowly cooled to 4° C., and the precipitated solid was filtered off. The product was washed with cold water (10 ml) and cold toluene (10 ml) and dried under reduced pressure at 40° C. 2.18 g (71.3 percent; content: 97.3 percent) of N-[5-(diphenylphosphinoylmethyl)-4-(4-fluorophenyl)-6-isopropylpyrimidin-2-yl]-N-methylmethanesulfonamide were isolated in the form of a colorless solid. The melting point of the product was 184° to 185° C.

EXAMPLE 9 (DIRECT REACTION)

N-[5-(Diphenylphosphinoylmethyl)-4-(4-fluorophenyl)-6-isopropylpyrimidin-2-yl]-N-methylmethanesulphonamide A suspension of 9.29 g (26.3 mmol) of [4-(4-fluorophenyl)-6-isopropyl-2-(N-methyl-N-methylsulfonylamino)pyrimidin-5-yl]methanol in 26 g of toluene was, with ice-bath cooling, admixed with 7.64 g (34.4 mmol) of chlorodiphenylphosphine. After rinsing with a little toluene, the mixture was heated at 111° C. for 2 h. After cooling to room temperature, 4.94 g of a 45 percent strength potassium hydroxide solution and 873 mg (2.71 mmol) of tetrabutylammonium bromide were added, and the mixture was stirred vigorously at 60° C. for 1 h. 100 ml of water was added to the warm reaction mixture. The mixture was briefly stirred at 60° C. and slowly cooled to 4° C., and the precipitated solid was filtered off. The product was washed with cold water (30 ml) and cold toluene (30 ml) and dried under reduced pressure at 40° C. 11.74 g (78.4 percent; content: 94.4 percent) of N-[5-(diphenylphosphinoylmethyl)-4-(4-fluorophenyl)-6-isopropylpyrimidin-2-yl]-N-methylmethanesulfonamide was isolated in the form of a colorless solid.

EXAMPLE 10 (DIRECT REACTION WITHOUT PHASE-TRANSFER CATALYST)

N-[5-(Diphenylphosphinoylmethyl)-4-(4-fluorophenyl)-6-isopropylpyrimidin-2-yl]-N-methylmethanesulphonamide 2.03 g (5.69 mmol) of [4-(4-fluorophenyl)-6-isopropyl-2-(N-methyl-N-methylsulfonylamino)pyrimidin-5-yl] methanol was initially charged in 13 g of toluene and, with ice-bath cooling, admixed with 1.69 g (7.60 mmol) of chlorodiphenylphosphine in 1.9 g of toluene. The mixture was heated at 109° C. for 2.5 h. After cooling to room temperature, the mixture was admixed with 1.09 g (8.74 mmol) of a 45 percent strength potassium hydroxide solution and stirred vigorously at 60° C. for 2 h, 45 min. 30 ml of water was added to the warm reaction mixture. The mixture was briefly stirred at 60° C. and slowly cooled to 4° C., and the precipitated solid was filtered off. The product was washed with cold water (10 ml) and cold toluene (10 ml) and dried under reduced pressure at 40° C. 2.44 g (76.8 percent; content: 99.1 percent) of N-[5-(diphenylphosphinoylmethyl)-4-(4-fluorophenyl)-6-isopropylpyrimidin-2-yl]-N-methylmethanesulfonamide was isolated in the form of a colorless solid.

EXAMPLE 11 (DIRECT REACTION)

N-[(5-Diphenylphosphinoylmethyl)-4-(4-fluorphenyl)-6-isopropylpyrimidin-2-yl]-N-methylmethanesulfonamide A solution of 60.08 g (0.170 mol) [4-(4-fluorophenyl)-6-isopropyl-2-(N-methyl-N-methylsulfonylamino)pyrimidin-5-yl]methanol in ca. 485 ml of toluene was admixed at 60° C. with 42.55 g (0.192 mol; content 99,7 percent) chlorodiphenylphosphine. The mixture was stirred for 2.5 h and then added to a mixture of 70.66 g of a 20 percent strength potassium hydroxide solution and 5.04 g (0.017 mol) tetrabutylammonium chloride at 60° C. The resulting reaction mixture was stirred for another 2 h at 60° C. Then 215 ml of water and 108 ml of toluene were added. The aqueous phase was separated off at 80° C. The organic phase was extracted twice with 2×215 ml of hot water. Residual water of the organic phase was removed azeotropicly. The mixture was slowly (2 h) cooled to 0° C. and the precipitated solid was filtered off. The product was washed twice with 2×160 ml of toluene and dried under reduced pressure at 40° C. 81.94 g (89.7 percent) of N-[(5-diphenylphosphinoylmethyl)-4-(4-fluorphenyl)-6-isopropylpyrimidin-2-yl]-N-methylmethanesulfonamide was isolated in the form of a colorless solid [content (HPLC): 100 percent].

What is claimed is:

1. A process for preparing N-[5-(diphenylphosphinoylmethyl)-4-(4-fluorophenyl)-6-isopropylpyrimidin-2-yl]-N-methylmethanesulfonamide of the formula:

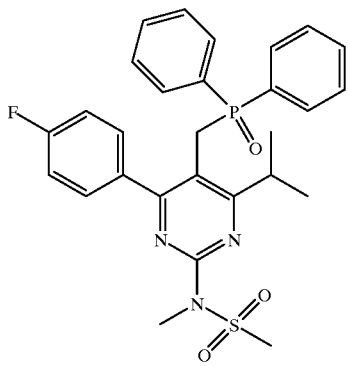

I characterized in that the [4-(4-fluorophenyl)-6-isopropyl-2-(N-methyl-N-methylsulfonylamino)pyrimidin-5-yl]methanol of the formula:

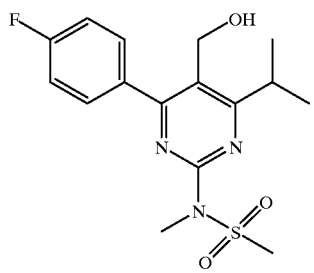

II is reacted with chlorodiphenylphosphine.

2. The process according to claim 1, wherein the [4-(4-fluorophenyl)-6-isopropyl-2-(N-methyl-N-methylsulfonylamino)pyrimidin-5-yl]methanol of the formula II is reacted directly with chlorodiphenylphosphine and subsequently with a base.

3. The process according to claim 1, wherein the [4-(4-fluorophenyl)-6-isopropyl-2-(N-methyl-N-methylsulfonylamino)pyrimidin-5-yl]methanol of the formula I is first deprotonated.

4. The process according to claim 3, wherein the deprotonation is carried out using an alkali metal hydride or an alkali metal hexaalkyldisilazane.

5. The process according to claim 4, wherein the reaction is carried out with the aid of a catalyst.

6. The process according to claim 5, wherein the catalyst used is iodine, an alkali metal iodide, an alkali metal halide or a dihaloalkane.

7. The process according to claim 6, wherein the reaction with chlorodiphenylphosphine is carried out at a temperature between 80° and 200° C.

8. The process according to claim 2, wherein the direct reaction with chlorodiphenylphosphine is carried out at a temperature between −20° and 130° C.

9. The process according to claim 8, wherein the base used is an alkali metal hydroxide.

10. The process according to claim 9, wherein the reaction is carried out with the aid of a phase transfer catalyst.

11. The process according to claim 3, wherein the reaction is carried out with the aid of a catalyst.

12. The process according to claim 3, wherein the catalyst used is iodine, an alkali metal iodide, an alkali metal halide or a dihaloalkane.

13. The process according to claim 3, wherein the reaction with chlorodiphenylphosphine is carried out at a temperature between 80° and 200° C.

14. The process according to claim 2, wherein the base used is an alkali metal hydroxide.

15. The process according to claim 8, wherein the reaction is carried out with the aid of a phase transfer catalyst.

16. The process according to claim 2, wherein the reaction is carried out with the aid of a phase transfer catalyst.

* * * * *